United States Patent [19]

Hansen et al.

[11] 3,955,573
[45] May 11, 1976

[54] ANTICOAGULANT DELIVERY DEVICE AND METHOD

[75] Inventors: A. Boyd Hansen; Gordon S. Reynolds, both of Bountiful, Utah

[73] Assignee: Sorenson Research Co., Inc., Salt Lake City, Utah

[22] Filed: Oct. 11, 1974

[21] Appl. No.: 514,055

[52] U.S. Cl. .............................. 128/276; 128/240
[51] Int. Cl.² .......................................... A61M 1/00
[58] Field of Search ........ 128/276, 277, 278, 350 R, 128/214 R, 240

[56] References Cited
UNITED STATES PATENTS

| | | | |
|---|---|---|---|
| 2,804,075 | 8/1957 | Borden | 128/277 |
| 3,512,517 | 5/1970 | Kadish et al. | 128/214 R X |
| 3,610,226 | 10/1971 | Albisser | 128/214 R X |
| 3,807,401 | 4/1974 | Riggle et al. | 128/277 |

Primary Examiner—Dalton L. Truluck
Attorney, Agent, or Firm—H. Ross Workman; J. Winslow Young

[57] ABSTRACT

An anticoagulant delivery device forming part of an aspiration wand and method for use in connection with autologous blood transfusion wherein an anticoagulant is delivered to and intimately mixed with aspirated blood in the vicinity of the aspiration tip of the wand.

11 Claims, 6 Drawing Figures

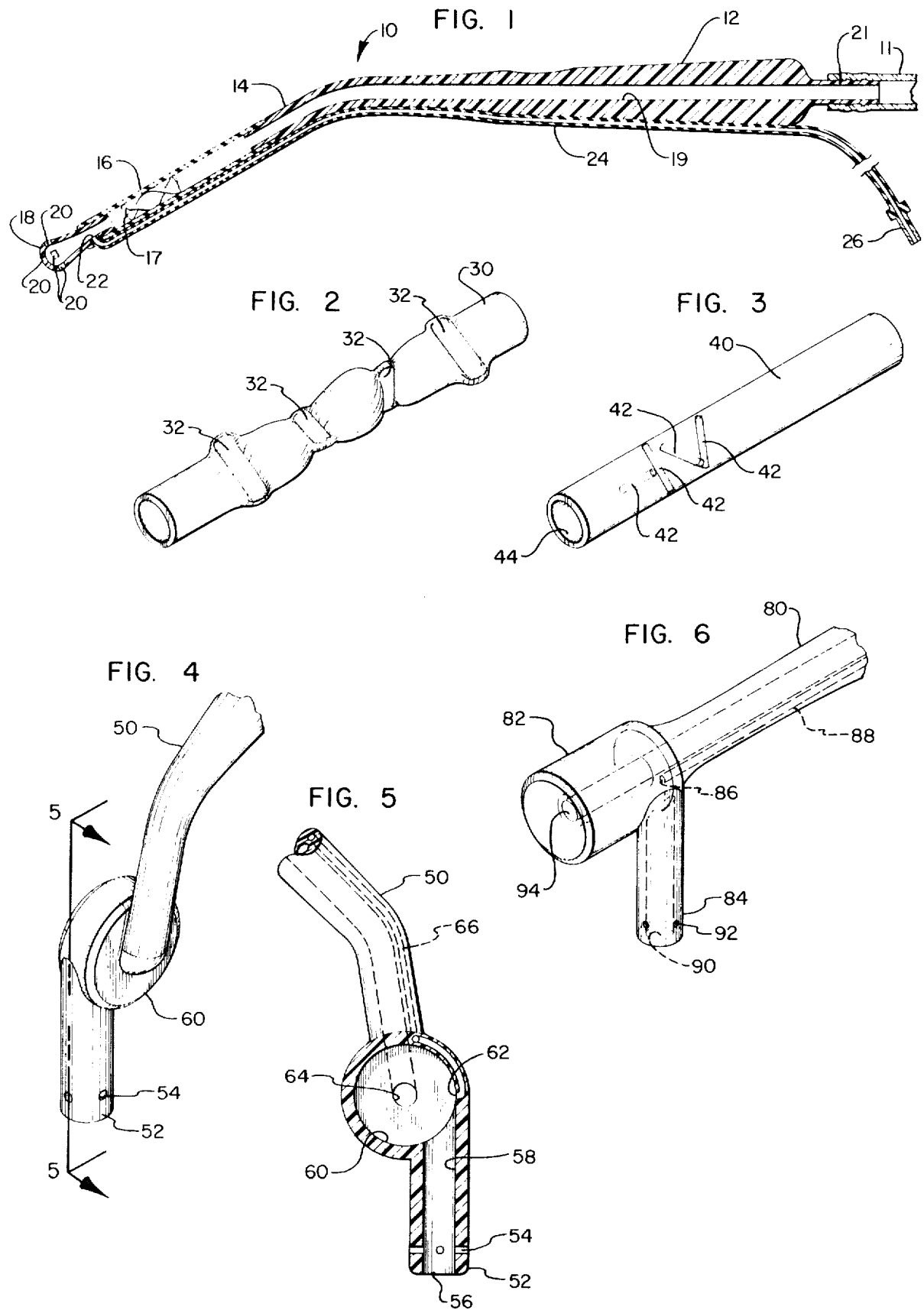

ANTICOAGULANT DELIVERY DEVICE AND METHOD

BACKGROUND

1. Field of the Invention

This invention relates to autologous blood transfusion and more particularly to an anticoagulant delivery device and method.

2. The Prior Art

Autologous blood transfusion is commonly defined as the return of the patient's blood to his own circulatory system during an active bleeding episode such as encountered in certain forms of surgery. It is well known that conventional homologous blood transfusion involves a high risk of hemagglutination, disease transfer and other undesirable side effects. Hemagglutination is minimized by lengthy and expensive blood cross-match procedures. Even with cross-matching, however, transfusion reactions are undesirably frequent. Presently, there is no known practical way of detecting and preventing transmittal of diseases such as hepatitis through homologous blood transfusion. Autologous blood transfusion has the distinct advantage in that adverse serum reactions are completely eliminated along with other problems suggested above associated with blood transfusions.

While blood replacement through autologous blood transfusion has been demonstrated to be safe and effective, routine use of this technique has not been established. One obvious reason for this failure is the lack of an effective, practical, inexpensive, and efficient method and apparatus for recovering and treating the blood for reinfusion.

During the collection phase, one of the most vital considerations is the prevention of coagulation of the aspirated blood. It is known that blood quickly commences to initiate coagulation upon exposure to the atmosphere or contact with a foreign body. Accordingly, devices for aspirating blood wherein anticoagulant is introduced into the blood at a substantial distance from the point of blood entry tend to permit unnecessary blood coagulation. An example of such a device is disclosed in U.S. Pat. No. 3,807,401.

Another system for preventing blood coagulation includes chamber anticoagulation which involves the constant surveillance and administration of anticoagulant to a collection chamber. This technique does not prevent clot formation in the vacuum line between the suction tip and the collection chamber. Further, devices which introduce rapid pressure change and/or abrade the blood cells cause hemolysis of the blood making it undesirable for reinfusion purposes.

Wands which are used to aspirate blood during surgery for removal to a remote container are well known in the art. They conventionally include a handle, aspiration tip and a long conduit into which a vacuum is introduced to draw aspirated blood to the container. Until this present invention, there has been no practical way to introduce anticoagulant into the blood without hemolysis or other undesirable side effects.

BRIEF SUMMARY AND OBJECTS OF THE INVENTION

The present invention avoids unnecessary coagulation of blood aspirated from the patient in conjunction with autologous blood transfusion. The invention includes an aspiration wand having a probe terminating in a perforated tip and including a mixing chamber adjacent the perforated tip. Anticoagulant is introduced into the aspirated blood at the tip and thoroughly mixed with the blood in the mixing chamber prior to transport through the suction line to a collection reservoir.

It is therefore an object of the present invention to provide improvements in the art of aspirating blood for autologous transfusion.

It is another object of this invention to provide an aspiration wand wherein an anticoagulant is delivered to the blood immediately upon aspiration.

An even still further object of this invention is to provide apparatus and method wherein anticoagulant is intimately mixed with the aspirated blood in a mixing chamber immediately adjacent the point of aspiration.

These and other objects and features of the present invention will become more fully apparent from the following description and appended claims taken in conjunction with the accompanying drawing.

BRIEF DESCRIPTION OF THE DRAWING

FIG. 1 is a longitudinal cross-sectional view of one presently preferred embodiment of the present invention.

FIG. 2 is a fragmentary perspective view of one embodiment of a baffle mixing chamber.

FIG. 3 is a fragmentary perspective view of another embodiment of a baffle mixing chamber.

FIG. 4 is a fragmentary perspective view of a vortex mixing chamber.

FIG. 5 is a cross-section view of the vortex mixing chamber of FIG. 4 taken along lines 5—5.

FIG. 6 is a perspective view of another embodiment of a vortex mixing chamber.

DETAILED DESCRIPTION OF THE PREFERRED EMBODIMENT

The invention is best understood by reference to the figures wherein like parts are designated with like numerals throughout.

The anticoagulant delivery unit disclosed herein is particularly useful in conjunction with the Aseptic Suction Collection System Method, U.S. patent application No. 408,895 filed Oct. 23, 1973. Of course, any suitable blood collection reservoir could be used with the illustrated embodiments of the invention. Blood aspirated through wand 10 is delivered by blood line 11 into the aforementioned receptacle for storage and later reinfusion into the patient according to acceptable techniques of autologous blood transfer.

The delivery unit, generally designated 10 includes a handle 12 and an integral probe 14. Probe 14 terminates in a rounded tip 18 having ports 20 therein. The handle 12, probe 14 and tip 18 define a continuous hollow passageway 19 traversing the entire length of the device 10. The handle 12 has a rearwardly projecting male coupling 21 onto which the conventional vacuum blood line 11 is press-fit. Probe 14 also includes a rounded mixing chamber 16 located in close proximity to the tip 18. The mixing chamber 16 is, in the illustrated embodiment, a cylindrical extension of the probe 14 and is hollow to permit internal mixing of blood and anticoagulant and subsequent transport of the blood to a container (not shown). In FIG. 1, the mixing chamber 16 is shown to be press-fit onto both the probe 14 and the tip 18. If desired, the mixing chamber can be an integral part of the probe and/or the tip 18. In the embodiment of FIG. 1, the mixing chamber 16 includes a baffle 17 which provides for mechanical mixing of blood aspirated through port 20 with an anticoagulant delivered through port 22. Baffle 17 provides a convoluted path, which accommodates thorough mixing but at the same time avoids significant pressure changes and cellular abrasion which tends to hemolyze blood cells.

Anticoagulant is delivered to wand 10 between the perforations 20 of tip 18 and mixing chamber 16 through the port 22 into which the terminal end of tubing 24 is mounted. Tubing 24 is connectable at fitting 26 to a source of a suitable anticoagulant (not shown) such as heparin. The tubing 24 is preferably attached to the exterior of device 10 along essentially its entire length so that tubing 24 is kept out of the way during surgery. If desired, the tubing 24 could be interposed through the hollow passageway 19 and anchored therein so that the open tip thereof is secured between the ports 20 and the mixing chamber 16. Further, the tubing 24 could be formed in the structure of the handle 12 and probe 14 as illustrated in FIG. 5 and described more particularly hereinafter.

To aspirate blood with wand 10, the operator, generally a surgeon or his assistant, activates a vacuum source (not shown) to impose a vacuum in line 11 and thereafter inserts tip 18 into blood which accumulates during surgery. The vacuum in line 11 draws blood through ports 20 of tip 18. Simultaneously, anticoagulant is delivered through port 22 into the blood and is thoroughly mixed therewith by passage over baffle 17 in mixing chamber 16. The treated blood is then transported along the passageway 19 and through blood line 11 to a suitable collection reservoir (not shown).

Referring now to FIG. 2, another embodiment for a mixing chamber as a section of a probe is shown at 30 and has integrally formed baffles 32. Baffles 32 are formed by laterally constricting the lumen of the mixing chamber, the plane of each restriction being oriented along a different axis. Blood and anticoagulant are thoroughly mixed by passing sequentially through each constricted baffle 32. In this manner a mixing chamber may be fabricated directly as an integral part of the probe 30, since constrictions in the walls of probe 30 form the necessary baffle system.

Referring now to FIG. 3, another embodiment for a mixing chamber 40 is shown wherein a plurality of rods 42 serve as baffles. Baffles or rods 42 transversely intersect the lumen 44 of mixing chamber 40 at various angular orientations. Blood and anticoagulant flowing through the lumen 44 are thereby thoroughly mixed. Clearly, any suitable baffle configuration could be used to mix the blood and anticoagulant in chamber 16.

Referring now to FIGS. 4 and 5, advantage is taken of the aforementioned negative pressure within the probe to create a vortex, the vortex serving to intimately mix anticoagulant with the aspirated blood. In this presently preferred embodiment of a vortex mixing chamber, probe 50 terminates in a tip 52 having ports 54 and an opening 56 therein. Opening 56 and ports 54 communicate with a tubular hollow 58 which tangentially intersects mixing chamber 60 so as to create the mixing vortex. Anticoagulant is delivered through a delivery tube 66 (shown in broken lines) to port 62 opening into the vortex mixing chamber 60. The delivery tube 66 is integrally formed in the structure of the probe 50 and associated handle (not shown). The port 62 opens into the mixing chamber 60 adjacent the intersection of the hollow 58 of tip 52. Aspirated blood and anticoagulant is swirled together in the mixing chamber 60 and thereafter withdrawn from vortex mixing chamber 60 through an axially aligned opening 64 which communicates directly with the hollow of probe 50.

Referring now to FIG. 6, another embodiment of a vortex mixing chamber 82 between probe 80 and perforated tip 84 is shown. Anticoagulant is delivered to the interior of mixing chamber 82 through a port 86 which is the terminal end of an anticoagulant delivery tube 88 (shown in broken lines). Blood aspirated through ports 90 and 92 of tip 84 passes tangentially into mixing chamber 82 and through the vortex action thus generated is intimately mixed with anticoagulant delivered through port 86. From mixing chamber 82 the mixed blood and anticoagulant passes through opening 94 thence through the hollow of probe 80 to the previously described collection apparatus.

It will be noted that in each of the foregoing embodiments of FIGS. 1 and 4 through 6 that anticoagulant is delivered to the blood in the immediate vicinity of the perforated tip before the blood reaches the mixing chamber. According to the present invention, the blood traverses only a very short distance before it is suitably treated with anticoagulant thereby greatly minimizing the opportunities for clot formation. The blood aspiration system of this invention is, therefore, a simple device which greatly simplifies the aspiration and treatment of blood with anticoagulant so that the blood is then suitable for autologous blood transfusion.

In the presently preferred embodiments of the present invention the handle, probe and mixing chamber are fabricated from medical grade plastic material so as to be easily fabricated, inexpensive, sterilizable, and disposable.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An anticoagulant delivery device for aspirating and treating blood comprising in combination:
   a hollow conduit, the hollow of the conduit having a vacuum applied thereto and defining a pathway for the transport of aspirated blood;
   a perforated tip joined to the conduit and comprising a passageway facilitating aspiration of blood into the hollow of the conduit;
   a mixing chamber comprising a housing having means for altering laminar flow of aspirated blood so as to create mixing turbulence therein, said mixing chamber being interposed between the conduit and the perforated tip; and
   means for delivering anticoagulant in the vicinity of the tip upstream from the mixing chamber whereby the anticoagulant is caused to be thoroughly mixed with the aspirated blood.

2. An anticoagulant delivery device as defined in claim 1 wherein said mixing chamber housing comprises means defining a cylindrical cavity having a diameter which is greater than the diameter of the conduit, and wherein said passageway of the perforated tip intersects the cylindrical cavity tangentially so that aspirated blood and anticoagulant form a vortex in the cavity.

3. An anticoagulant delivery device as defined in claim 1 wherein said mixing chamber comprises at least one baffle to develop turbulance sufficient to mix the aspirated blood and anticoagulant.

4. An anticoagulant delivery device as defined in claim 1 wherein said anticoagulant delivery means comprises a tube mounted exterior of the conduit.

5. An anticoagulant delivery device as defined in claim 1 wherein said anticoagulant delivery means comprises a tube carried within the conduit and terminating in a discharge port rigidly secured adjacent the junction of the tip and mixing chamber housing.

6. An anticoagulant delivery device as defined in claim 1 wherein said mixing chamber housing is an initially separate segment having a coupling site at each end, one end being joined to the conduit and the other end to the perforated tip.

7. An anticoagulant delivery device as defined in claim 1 wherein said mixing chamber housing and said conduit are integrally joined into a one-piece unit.

8. A method of combining aspirated blood from a patient with anticoagulant in a hollow conduit, the conduit comprising a hollow perforated tip and a mixing chamber immediately downstream from the tip comprising the steps of:

connecting the conduit to a vacuum source so as to provide negative pressure at the perforated tip;

delivering an anticoagulant to the conduit in the vicinity of the tip and upstream from the mixing chamber; and inserting the tip into a blood source thereafter forcing the blood and anticoagulant over a convoluted path in the mixing chamber to create turbulent flow and mix anticoagulant with the blood prior to its traversal through the conduit so asa to minimize clotting of the blood in the conduit.

9. A method of combining aspirated blood with anticoagulant as defined in claim 8 wherein said mixing step comprises creating a vortex of blood and anticoagulant upon aspiration of the blood and prior to traversal through the conduit.

10. A method of combining aspirated blood with anticoagulant as defined in claim 8 wherein said mixing step comprises channelling blood and anticoagulant across a tortuous path defined by at least one baffle.

11. An anticoagulant delivery device for aspirating and treating a patient's blood comprising:

an aspiration wand having a perforated leading tip and a handle joined to the tip, the handle and tip presenting an elongated blood-carrying conduit and means for imposing a vacuum at the perforated tip and along the conduit;

means for delivering anticoagulant from a remote source to the wand near the tip; and a mixing chamber mounted upon the handle downstream from the tip, the mixing chamber having a housing comprising means for significantly increasing turbulence within the conduit so as to intimately mix the anticoagulant and aspirated blood after the blood enters the tip of the wand.

* * * * *